US012584886B2

(12) United States Patent
Theuss et al.

(10) Patent No.: US 12,584,886 B2
(45) Date of Patent: Mar. 24, 2026

(54) SEMICONDUCTOR DEVICE FOR MEASURING HYDROGEN AND METHOD FOR MEASURING A HYDROGEN CONCENTRATION

(71) Applicant: Infineon Technologies AG, Neubiberg (DE)

(72) Inventors: Horst Theuss, Wenzenbach (DE); Rainer Markus Schaller, Aichen (DE)

(73) Assignee: Infineon Technologies AG, Neubiberg (DE)

( * ) Notice: Subject to any disclaimer, the term of this patent is extended or adjusted under 35 U.S.C. 154(b) by 329 days.

(21) Appl. No.: 18/496,420

(22) Filed: Oct. 27, 2023

(65) Prior Publication Data

US 2024/0151689 A1      May 9, 2024

(30) Foreign Application Priority Data

Nov. 3, 2022    (DE) .......................... 102022211627.5

(51) Int. Cl.
*G01N 29/036*        (2006.01)
*G01N 27/22*         (2006.01)
*G01N 33/00*         (2006.01)

(52) U.S. Cl.
CPC ......... *G01N 29/036* (2013.01); *G01N 27/227* (2013.01); *G01N 33/0027* (2013.01); *G01N 2291/014* (2013.01); *G01N 2291/021* (2013.01)

(58) Field of Classification Search
CPC ............... G01N 29/036; G01N 27/227; G01N 33/0027; G01N 2291/014; G01N 2291/021; G01N 33/005
See application file for complete search history.

(56) References Cited

U.S. PATENT DOCUMENTS

| | | | |
|---|---|---|---|
| 4,926,155 A | 5/1990 | Colla et al. | |
| 8,139,905 B1 * | 3/2012 | Bazzone ................ G01K 13/08 | |
| | | | 398/79 |
| 12,209,975 B2 * | 1/2025 | Magana ............. G03F 7/70916 | |
| 2005/0262943 A1 | 12/2005 | Claydon et al. | |
| 2017/0343522 A1 | 11/2017 | Ikehashi et al. | |
| 2021/0102919 A1 | 4/2021 | Schlicke et al. | |
| 2022/0011254 A1 | 1/2022 | Hayashi | |
| 2022/0074897 A1 * | 3/2022 | Eberl ................. G01N 29/4427 | |
| 2024/0053281 A1 * | 2/2024 | Magana ............. G03F 7/70916 | |

FOREIGN PATENT DOCUMENTS

| | | |
|---|---|---|
| DE | 102014105861 A1 | 10/2015 |
| DE | 102014010116 B4 | 11/2018 |
| DE | 102019217465 A1 | 5/2021 |
| EP | 2840372 A1 | 2/2015 |
| EP | 3936852 A1 | 1/2022 |
| JP | 2021001881 A | 1/2021 |
| KR | 20180074100 A | 7/2018 |

* cited by examiner

*Primary Examiner* — Francis C Gray
(74) *Attorney, Agent, or Firm* — Harrity & Harrity, LLP

(57)                ABSTRACT

The application relates to a semiconductor device (20) for measuring hydrogen including a sensor chip (10), which has a sensor including a sensor layer (14), which changes its mechanical stress upon contact with hydrogen, wherein the sensor is configured to detect the change in the mechanical stress of the sensor layer (14) by way of a membrane (15), wherein for detection purposes provision is made for exciting the membrane (15) using a periodic signal. The application furthermore relates to a method for measuring a hydrogen concentration.

17 Claims, 6 Drawing Sheets

SEMICONDUCTOR DEVICE FOR MEASURING HYDROGEN AND METHOD FOR MEASURING A HYDROGEN CONCENTRATION

CROSS-REFERENCE TO RELATED APPLICATION

This application claims priority to German Patent Application No. 102022211627.5 filed on Nov. 3, 2022, the content of which is incorporated by reference herein in its entirety.

TECHNICAL FIELD

The application relates to a semiconductor device for measuring hydrogen and to a method for measuring a hydrogen concentration in a medium using such a semiconductor device.

BACKGROUND

Measurement of hydrogen is important for various fields of application. There are safety aspects, in that for example the concentration of hydrogen has to be measured in order to recognize whether an oxyhydrogen explosion may occur. However, in other applications, too, it is advantageous to detect the hydrogen concentration or amount of hydrogen in order to ensure a technical functionality for which the hydrogen is used.

It is an object to provide an improved device and an improved method for measuring hydrogen.

This object is achieved using the combinations of features in the independent patent claims.

SUMMARY

A semiconductor device for measuring hydrogen including a sensor chip is proposed, wherein the sensor chip has a sensor including a sensor layer, which changes its mechanical stress upon contact with hydrogen. The sensor is configured to detect the change in the mechanical stress of the sensor layer by way of a membrane, wherein for detection purposes provision is made for exciting the membrane using a periodic signal. A sensor layer that changes its mechanical stress upon contact with hydrogen is also referred to as a hydrogen-active sensor layer. The membrane has thin structures which have a large areal extent in relation to their thickness. The membrane has an area having the ability to oscillate. The change in the mechanical stress of the sensor layer can change properties of the membrane, e.g., strength, stiffness, modulus of elasticity, elastic constants, electrical properties. This change in at least one property of the membrane can be detected well using the excitation of the membrane with the periodic signal, by virtue of e.g., the accuracy of the measurement being improved and/or the measurement being made possible in the first place using the excitation.

Furthermore, a method for measuring a hydrogen concentration in a medium using such a semiconductor device is proposed, wherein the sensor layer is contacted with the medium in a first step, and the change in stress of the sensor layer is detected using the sensor in a second step.

A semiconductor device is understood to mean a device which has the sensor chip, but also the construction on which the sensor chip is applied. Furthermore, the semiconductor device also includes a cavity housing possibly present and/or a mold compound and electrical terminals or other attachments. The semiconductor device can thus be understood to mean for example a device which could be sold thus as a hydrogen sensor. Particularly advantageously, a hydrogen measurement can be accomplished by a sensor chip produced substantially from semiconductor, which sensor chip can easily be produced reliably and at reasonable cost in large numbers.

Such a sensor chip has a sensor including a sensor layer, which changes its mechanical stress upon contact with hydrogen. In other words, this exploits the effect that in the case of some materials hydrogen can change the mechanical stress in a layer, e.g., owing to diffusion and/or adsorption. The sensor layer consists of an $H_2$-active material. An $H_2$-active material develops mechanical stresses as a consequence of $H_2$ diffusion and/or $H_2$ adsorption. Examples of such materials are Pd, Pt, Y, or alloys including Pd, Pt, Y as base material. However, ferrite, specific silicon structures or Si nitrides also exhibit the effect. A further group of $H_2$-active materials which can be used for the sensor layer has so-called swelling effects upon contact with hydrogen. This group includes e.g., indium(III) oxide or tin(IV) oxide.

The sensor of the sensor chip detects the change in the mechanical stress of the sensor layer by way of a membrane, which is excited by a periodic signal for detection purposes. For this purpose, the sensor layer is applied e.g., on the membrane. In this case, the sensor layer can partly or completely cover the membrane. It is likewise possible for the sensor layer to project beyond the edge of the membrane. A change in the mechanical stress of the sensor layer changes at least one property of the membrane on which the sensor layer is applied. For the purpose of detecting the mechanical stress change, the sensor can have an electrical circuit besides the sensor layer, which electrical circuit periodically excites the membrane and outputs a changed electrical signal, e.g., a voltage or a current, depending on the change in the at least one property of the membrane.

The sensor chip can be configured in particular as a MEMS chip. A MEMS chip (MEMS=MicroElectroMechanical System) is a component which combines logic elements and micromechanical structures in one chip. A MEMS chip can process mechanical and electrical information and can have very small structures in the micrometers range. In some implementations, the sensor chip can have a MEMS structure with membrane, which is excited by a periodic signal in the form of an electrical AC voltage for the purpose of capacitive pressure measurement or which is excited by a periodic signal in the form of an oscillation for the purpose of detecting the deflection of the membrane. Sensor chips based on MEMS microphones or MEMS pressure sensors can thus be used for measuring hydrogen.

The sensor can e.g., be configured to cause the membrane to oscillate using the periodic signal for the purpose of detecting the change in the mechanical stress. An oscillation corresponds to a periodic spatial deflection of the membrane. The sensor can then detect an oscillation property of the membrane which changes with the change in the mechanical stress of the sensor layer applied on the membrane. For this purpose, the sensor can detect in particular a change in the resonant frequency and/or a change in a Q-factor of the membrane, both of which may be dependent on the change in the mechanical stress of the sensor layer. The Q-factor, also called quality factor, is a measure of the degree of damping of the oscillation. If the maximum amplitude is plotted against various oscillation frequencies, then a high-Q membrane has a defined peak at a specific frequency, similar to an undamped oscillation. With a lower Q-factor, the peak is wider and not as high overall. By way of a change in the Q-factor, it is possible—just like by way of a change in the resonant frequency—to determine the change in the mechanical stress of the sensor layer applied on the membrane.

In one implementation, the membrane is part of the capacitance. The sensor is configured to detect a change in the capacitance. In this case, the change in the capacitance is dependent on the change in the mechanical stress of the sensor layer applied to the membrane. In particular, the sensor can be configured to excite the membrane by applying an AC voltage to the capacitance for the purpose of detecting the change in the capacitance. This method detects the capacitance by way of a capacitive AC current measurement.

In some implementations, the membrane forms an electrode of the capacitance and the sensor has at least one counter-electrode with respect to the membrane. The counter-electrode, called backplate, can be stationary and rigid in relation to the membrane. The counter-electrode can be perforated, that is to say, it can have passages. By way of the counter-electrode, the detection of the change in the properties of the membrane as a result of the influence of hydrogen can be detected better, by virtue of e.g., a capacitance measurement between membrane and counter-electrode being carried out.

The membrane can also be arranged between two counter-electrodes, the membrane itself then not constituting an electrode of the capacitance. In some implementations, the membrane can also be configured as an electrode of the capacitance in addition to the two counter-electrodes.

In further example implementations, the at least one counter-electrode is arranged between the membrane and a further membrane. In this case, the membrane and/or the further membrane can optionally be configured as an electrode of the capacitance. The sensor layer is applied on the membrane, and in some implementations on the further membrane a further sensor layer is applied, which changes its mechanical stress upon contact with hydrogen.

It is furthermore proposed that the detection of the change in the mechanical stress is effected by comparison with a further sensor, wherein the further sensor differs from the sensor in terms of construction in regard to the sensor layer. In some implementations, both the sensor and the further sensor can each have a membrane. The further sensor can differ from the sensor e.g., in that its membrane does not have a sensor layer, or else has a layer that does not react to contact with hydrogen. Using comparative measurements on both sensors, the change in the mechanical stress of the membrane of the sensor can then be determined precisely.

Furthermore, a construction of the semiconductor device is proposed which affords the sensor protection against further mechanical stresses. In this case, provision can be made for affording the sensor, in particular the sensor layer, protection against further mechanical stresses. The construction of the semiconductor device is configured such that it affords the sensor protection against further mechanical stresses. These further mechanical stresses are undesired for the measurement, e.g., are not induced by hydrogen on or in the sensor layer. The further mechanical stresses can be induced for example by way of the construction or the securing of the semiconductor device and can thus influence a hydrogen measurement according to the present measurement principle, which is not desired.

In some implementations, the semiconductor device has one or more plastically and/or elastically deformable components which afford the sensor protection against further mechanical stresses. These components are configured to keep these undesired mechanical stresses away from the sensor or at least to damp them considerably, such that these further mechanical stresses have no significant influence on the measurement of the hydrogen or of the hydrogen concentration. The plastically or elastically deformable components can be configured e.g., as a stress decoupling structure on the chip and/or a low-stress construction of the semiconductor device.

Moreover, in some implementations, the sensor chip furthermore has a substrate, on which the sensor is fitted, wherein the deformable components have one or more trenches in the substrate which at least partly surround the sensor. This trench enables the undesired mechanical stresses to be guided past the sensor, mechanically short-circuited or at least damped. The deformation of the trench absorbs elastic stress, for example, and then releases it again toward the outside. However, it is also possible for a plastic deformation to take place, which then converts the absorbed mechanical stress into deformation energy. Such trenches can be produced using suitable patterning technologies in semiconductor engineering. By way of example, the trenches can be produced by etching, either dry- or wet-chemical. The trench or trenches need not completely surround the sensor, rather partial surrounding by the trench is also sufficient.

The substrate is for example undoped silicon or silicon dioxide or other electrically insulating materials.

In some implementations, provision is made of a cavity housing having an opening, via which the cavity formed by the cavity housing is connected to the surroundings (e.g., an environment surrounding the semiconductor device), wherein the deformable components include a wiring of the sensor chip. In this case, the cavity and the surroundings can have a gaseous medium. In this case, the hydrogen measurement is intended to measure hydrogen molecules present in the medium. In this case, provision is made for the hydrogen molecules to pass in the direction of the sensor layer via the opening. The term wiring is taken to mean the electrical connections, for example applied lines or else bond wires, which electrically supply the sensor and transfer signals.

Furthermore, in some implementations, provision is made of a cavity housing having an opening, via which the cavity is connected to the surroundings, wherein the deformable components include an adhesive connection of the sensor chip, in some implementations of the substrate of the sensor chip, to a wall of the cavity housing. This adhesive connection enables reliable, permanent connections of parts to be connected, without thermal energy being supplied. The adhesive connection can be configured as soft, in some implementations, so that it affords protection against further mechanical stresses.

Furthermore, in some implementations the construction of the semiconductor device has potted regions of the sensor chip with an exposed sensor layer, wherein the coefficient of thermal expansion of the mold compound is chosen such that it affords the sensor protection against thermally induced further mechanical stresses. In this case, the mold compound can include e.g., a resin, such as, for example, a casting resin.

In order to produce such a semiconductor device in which the construction of the semiconductor device has potted regions of the sensor chip with an exposed sensor layer, and in which the coefficient of thermal expansion of the mold compound is chosen such that it affords the sensor protection against thermally induced further mechanical stresses, it is possible to choose e.g., a film assisted molding method or a pin molding method.

BRIEF DESCRIPTION OF THE DRAWINGS

Example implementations are illustrated in the drawing and are explained in greater detail in the following description.

In the Figures.

In the Figures, the same reference signs are used for identical or similar elements. The illustration in the Figures need not be to scale.

DETAILED DESCRIPTION

Figure 1:
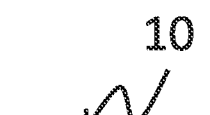
FIG. 1 shows a schematic sectional illustration of a first example implementation of the sensor chip.
Figure 1:
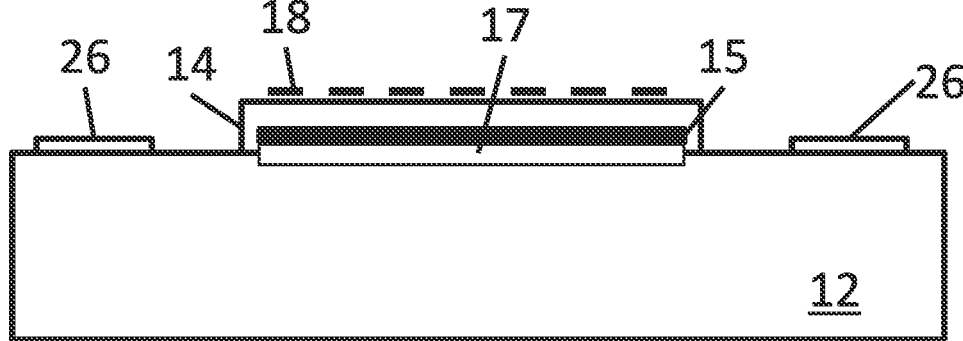

FIG. 1 shows a sensor chip 10 comprising a substrate 12. Contact pads 26 consisting of a metal layer or a metal layer system comprising copper, for example, are applied on each of the outer areas of the substrate 12. A membrane 15 with a hydrogen-active sensor layer 14 is fitted over a cavity 17. A catalytic layer 18 is optionally provided over the sensor layer 14. The catalytic layer 18 comprises catalytic material, e.g., palladium. The catalytic layer 18 is suitable for catalyzing the dissociation of $H_2$ molecules into atoms and/or ions.

Upon contact between hydrogen and the sensor layer 14, the mechanical stress of the sensor layer 14 changes. Associated with that, at least one property changes at the membrane 15. This change is detected by the sensor by virtue of the latter exciting the membrane 15 using a periodic oscillation. In this case, the cavity 17 can enable a mechanical oscillation of the membrane 15. By detecting oscillation properties of the membrane 15, it is then possible to determine the change in the mechanical stress of the sensor layer 14 and thus the hydrogen concentration. In particular, a resonant frequency of the oscillation of the membrane 15 can be detected. The action of hydrogen on the sensor layer 14 causes a change in the mechanical stress thereof and hence in the mechanical properties of the membrane 15, e.g., the resonant frequency thereof. The hydrogen concentration can be deduced by detecting a change in the resonant frequency of the membrane 15.

It is also possible to use electrical properties of the cavity, e.g., when the membrane 15 is excited by AC voltage. The change in the mechanical stress of the sensor layer 14 and the attendant changed properties of the membrane 15 result in changes in the capacitance of the microsystem comprising membrane 15 and cavity 17. Such changes in capacitance can be determined by AC current capacitance measurement with the membrane 15 being excited by AC voltage, and the hydrogen concentration can be deduced as a result.

The sensor chip 10 can be configured e.g., as a MEMS structure. A MEMS structure has logic elements and micromechanical structures, such as in the present case e.g., the membrane 15 and the cavity 17. The thickness of the cavity 17 can be e.g., in the nanometers to micrometers range. The size of the MEMS chip can be in the millimeters range. Production can be effected e.g., using surface micromachining and/or bulk micromachining. In the case of surface micromachining, structures are produced on the top side of the substrate 12 using a sequence of thin-film deposition and selective etching. In the case of bulk micromachining, structures are produced within the substrate 12 using selective etching.

Figure 2:
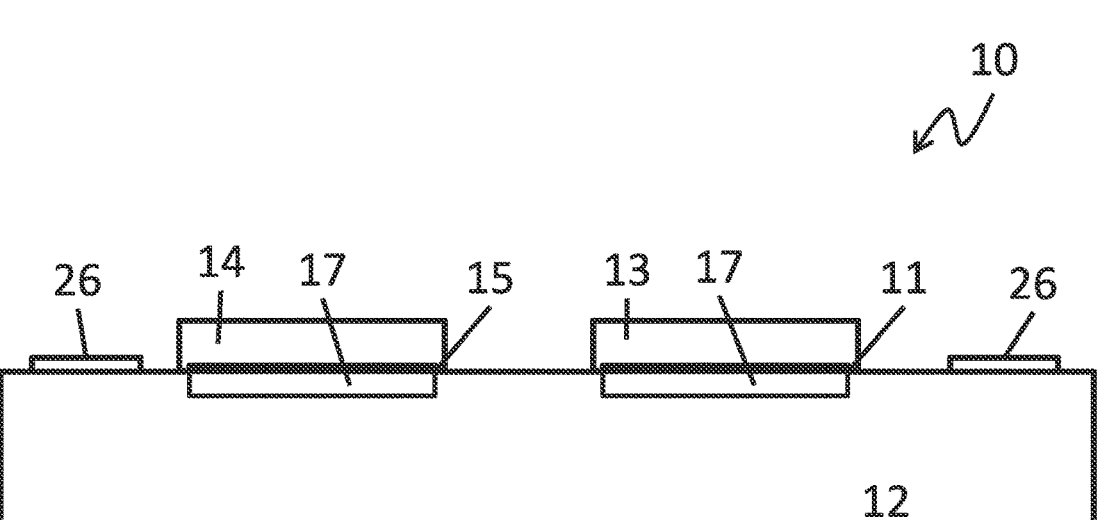
FIG. 2 shows a schematic sectional illustration of a second example implementation of the sensor chip.

FIG. 2 shows the sensor chip 10 comprising the substrate 12 and the contact pads 26. In the implementation illustrated, on the left-hand side, the membrane 15 and the sensor comprising the sensor layer 14 are arranged over the cavity 17. A second membrane 11 with a further layer 13 is arranged over the cavity 17 on the right-hand side. The layer 13 is not hydrogen-active. Upon contact between the sensor chip 10 and hydrogen, the hydrogen concentration can then be determined using comparative measurements on both membranes 11, 15. The measurement principles described above can find application here. The sensor layer 14 can optionally have a catalytic layer 18.

Figure 3:
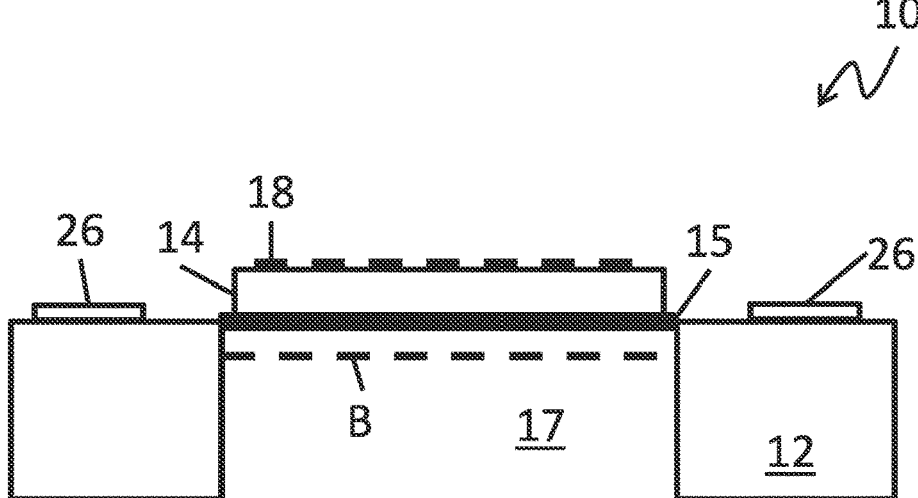
FIG. 3 shows a schematic sectional illustration of a third example implementation of the sensor chip.

FIG. 3 shows the sensor chip 10 comprising the contact pads 26 applied on the substrate 12. The membrane 15 with the hydrogen-active sensor layer 14 is fitted over the cavity 17. The catalytic layer 18 is optionally provided on the sensor layer 14. The construction illustrated can be configured similarly to a MEMS microphone with a membrane 15 and perforated stationary counterelectrode B. By way of the counterelectrode, the detection of the change in the mechanical properties of the membrane 15 as a result of the action of hydrogen on the sensor layer 14 can be detected better, e.g., by measurement of a change in capacitance between membrane 15 and counterelectrode B.

A realization with the optional catalytic layer 18 is possible in all the example implementations shown.

Figure 4:
FIG. 4 shows a schematic sectional illustration of a fourth example implementation of the sensor chip.
Figure 4:
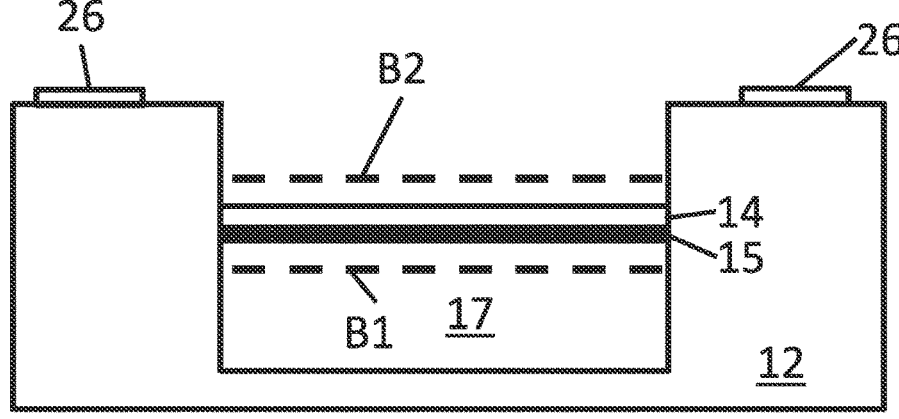

FIG. 4 shows the sensor chip 10, in which the membrane 15 with the sensor layer 14 is arranged between two counterelectrodes B1, B2. Like the counterelectrode B in FIG. 3, these counterelectrodes B1, B2 can be configured such that they are perforated and stationary in relation to the membrane 15. In this implementation, the membrane 15 can optionally likewise be configured as an electrode. A detection of the change in the at least one property of the membrane 15 as a result of the action of hydrogen on the sensor layer 14 affects the capacitance formed by the membrane 15 and the counterelectrodes B1, B2. By way of an excitation of the membrane 15 by AC voltage, the change in capacitance can then be detected using the counterelectrodes B1, B2.

Figure 5:
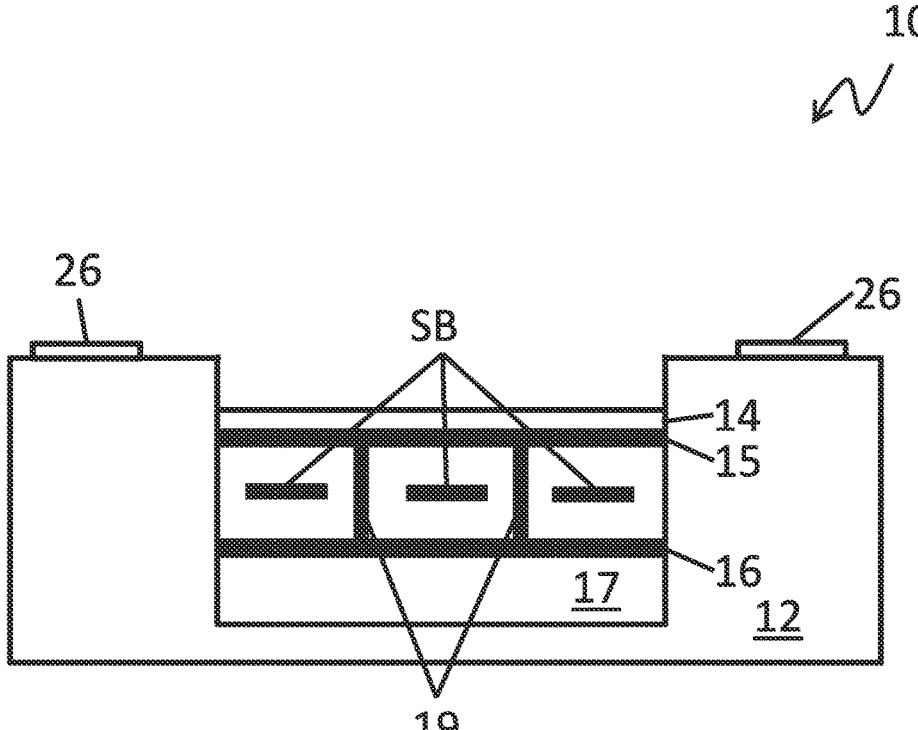
FIG. 5 shows a schematic sectional illustration of a fifth example implementation of the sensor chip.

FIG. 5 shows the sensor chip 10 as a MEMS chip with membrane 15 and sensor layer 14 fitted thereon. The membrane 15 and the sensor layer 14 are arranged in a cavity 17 of the sensor chip 10. A further membrane 16 is likewise arranged in the cavity 17. The construction illustrated is similar to a MEMS microphone structure. The structure uses two movable membranes 15, 16, which are mechanically coupled by electrically insulating columns, of the sealing 19. A differentiated detection of the measurement values is made possible by the sealing 19. The counterelectrode SB is fitted between the membrane 15 and the further membrane 16. The counterelectrode SB has passages. In this case, the columns of the sealing 19 run through these passages of the counterelectrode SB. The pressure can be reduced between the two membranes 15, 16 where the counterelectrode SB is fitted.

Figure 6:
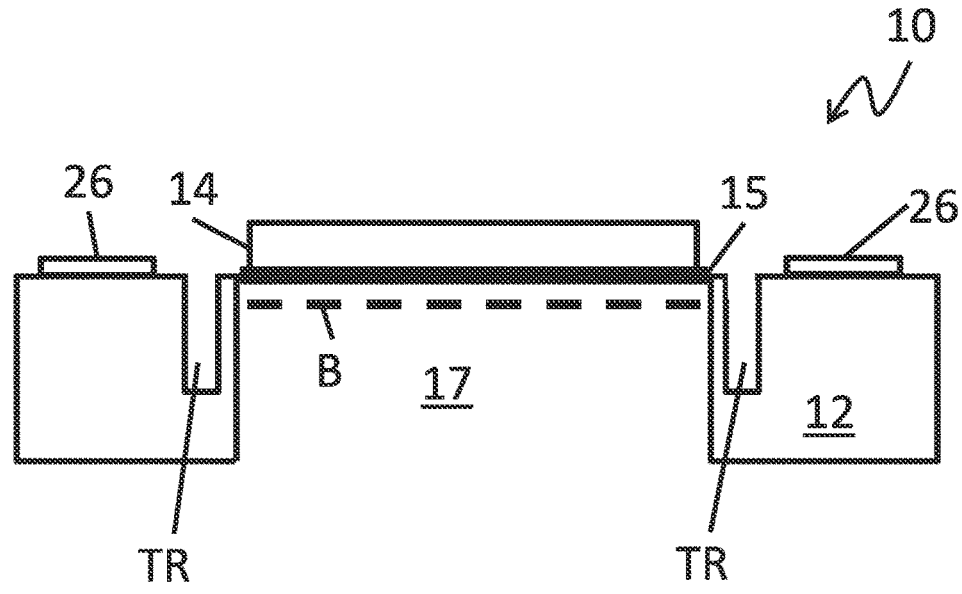
FIG. 6 shows a first schematic sectional illustration of a sixth example implementation of the sensor chip.

FIG. 6 shows the sensor chip 10 comprising the substrate 12, into which one, two or more trenches TR have been introduced by patterning measures from semiconductor engineering. In actual fact, it is also possible for there to be just a single trench TR, leading for example around the sensor comprising the sensor layer 14. For example, the sensor comprising the sensor layer 14 can be surrounded by deep trenches TR, e.g., in interleaved "L-shapes". In another implementation, the trenches TR form a springlike structure that completely surrounds the sensor comprising the sensor layer 14. Consequently, the sensor comprising the sensor layer 14 is resiliently coupled to the surrounding substrate mass 12.

Contact pads 26 consisting of a metal layer or a metal layer system comprising copper, for example, are applied on each of the outer areas of the substrate 12. In the center, the sensor layer 14 with the membrane 15 and the counterelectrode B can be seen above the cavity 17 in the substrate 12.

Figure 7:
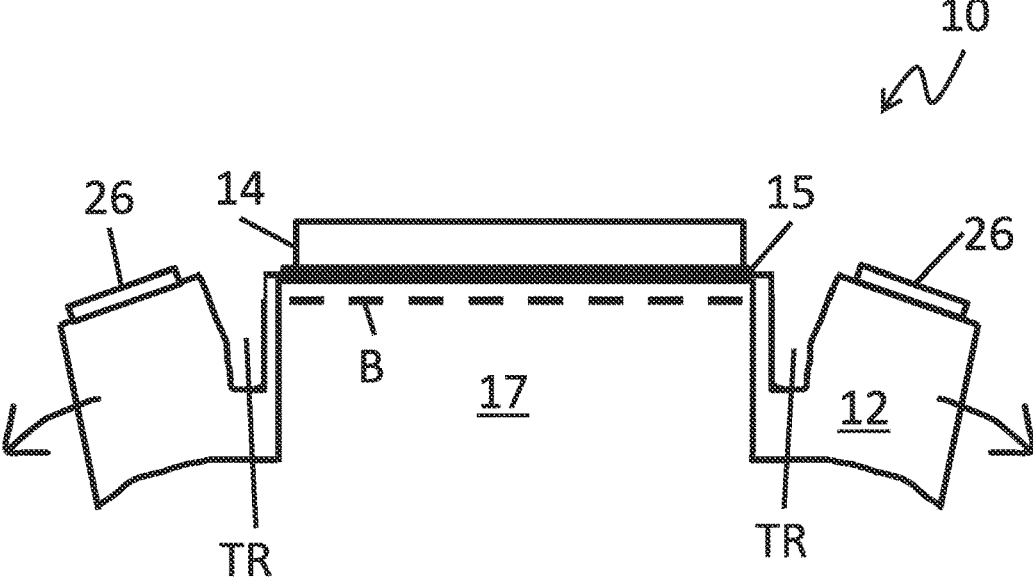
FIG. 7 shows a second schematic sectional illustration of the sixth example implementation of the sensor chip.

The implementation of the sensor chip 10 comprising the trenches TR that is shown in FIGS. 6 and 7 is also applicable to the other implementations of the sensor chip 10 shown in FIGS. 1 to 5.

FIG. 7 illustrates the sensor chip 10 from FIG. 6 under undesired mechanical stress. It is evident that the outer regions of the substrate 12 with the contact pads 26 bend to the side. This is made possible by the trenches TR. The mechanical stress, which was induced externally either mechanically or thermally, is thus kept away from the sensor comprising the sensor layer 14, thereby avoiding or reducing an influence on the measurement.

Figure 8:
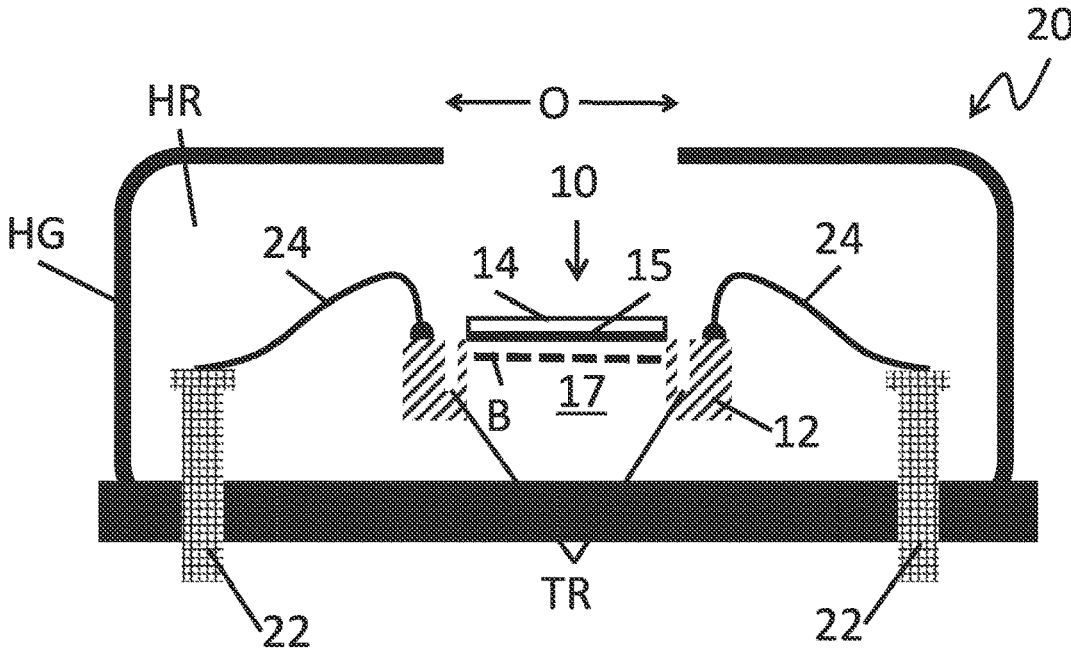
FIG. 8 shows a schematic illustration of one implementation of the semiconductor device with a schematically illustrated sensor chip and cavity housing.

FIG. 8 shows a semiconductor device 20 in a schematic sectional illustration. In this case, provision is made of a cavity housing HG having an opening O centrally toward the top. Through this opening O, the hydrogen can then pass to the sensor layer 14. The sensor chip 10 is arranged centrally below the opening O. However, it could also be arranged offset with respect thereto. In the event of hydrogen arising, ingress of the hydrogen then occurs in the cavity HR. The sensor chip 10 comprising the sensor layer 14 can then detect the hydrogen as intended by way of an excitation of the membrane 15.

The substrate 12 once again has the trenches TR or the trench TR, a respective bonding connection 24 being led to a respective contact 22 via the contact pads 26. Optionally, the implementation illustrated in FIG. 8 can also be implemented without the trench TR.

It is possible—and this also applies to the other figures—for more than two contact pads 26 to be provided, and also correspondingly a plurality of further bonding connections 24. That is the case particularly if more complex circuits are provided for the sensor.

Via the bonding connections 24, it is possible to supply the sensor chip 10 with electrical energy and/or to transfer signals.

Figure 9:
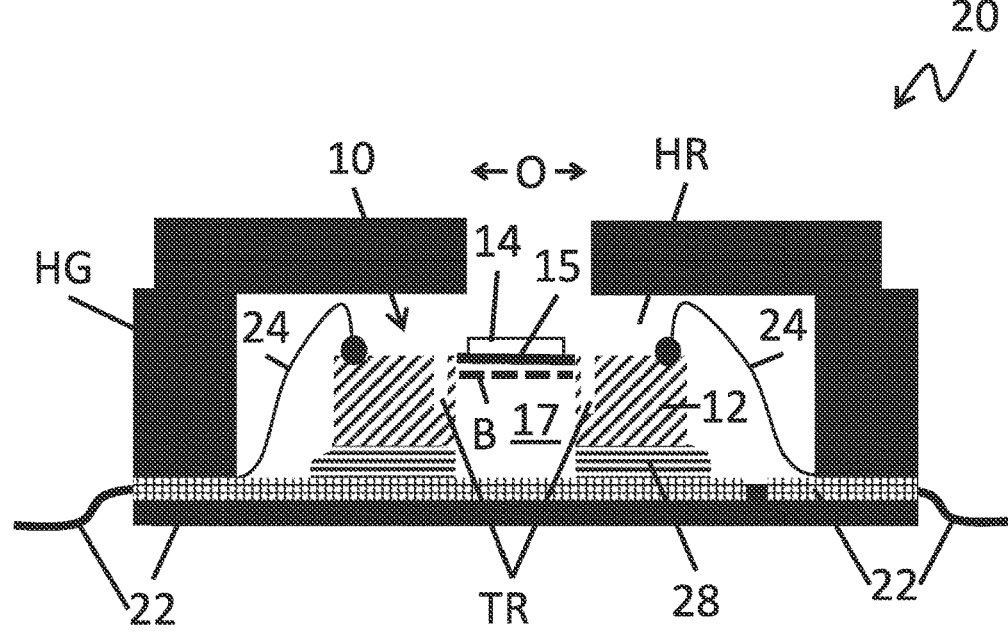
FIG. 9 shows a schematic illustration of a further implementation of the semiconductor device with a cavity.

FIG. 9 shows an alternative implementation to FIG. 8. The semiconductor device is once again designated by 20, and there is likewise the cavity housing HG and the cavity HR and also the opening O. The substrate 12 having the trench TR and also the sensor chip 10 comprising the sensor layer 14 are likewise illustrated. Via the bonding connections 24, an electrical connection to the outside world is again established via the contact 22. Furthermore, an adhesive layer 28 is provided, onto which the sensor chip 10 is adhesively bonded in order to be connected to the housing HG. The adhesive layer 28 is preferably configured as soft, so that it can afford the sensor chip 10 protection against further mechanical stresses.

The hydrogen can once again penetrate into the cavity HR through the opening O, and the sensor comprising the sensor layer 14 can then detect the hydrogen concentration by way of the excited membrane 15 in accordance with its effect. As in other implementations, a calibration is advantageous in this case.

The substrate 12 once again has the trenches TR or the trench TR, a respective bonding connection 24 being led respectively to a contact 22 via the contact pads 26. Optionally, the implementation illustrated in FIG. 9 can also be implemented without a trench TR.

Figure 10:
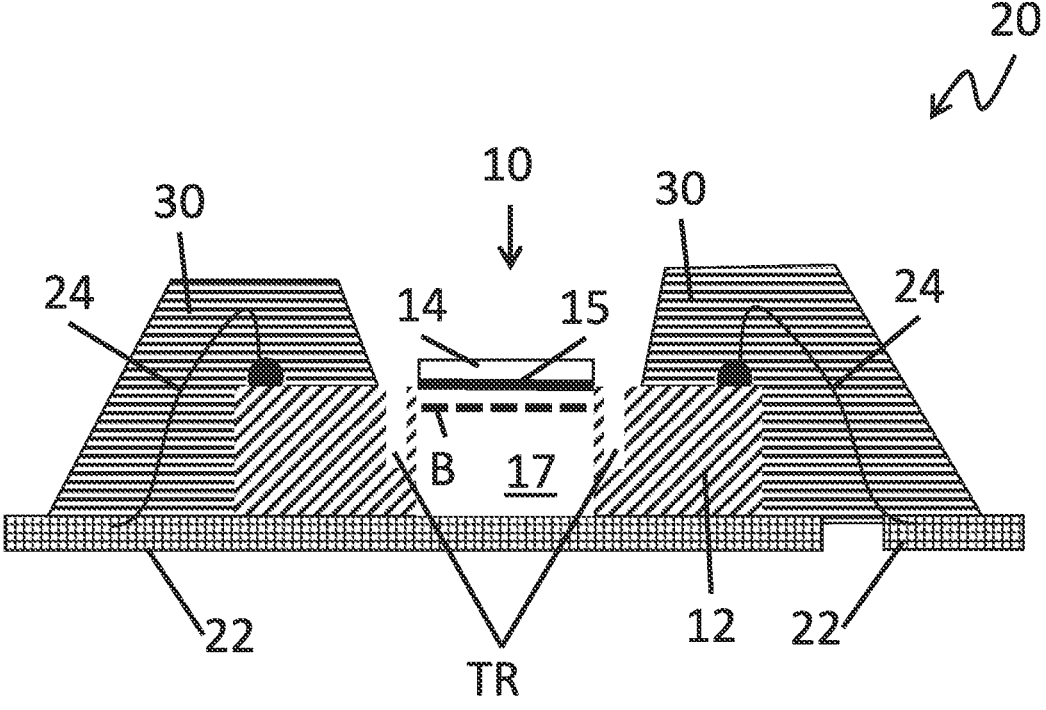
FIG. 10 shows a schematic illustration of the semiconductor device with a mold compound.

FIG. 10 shows a further illustration of the semiconductor device 20 comprising the sensor chip 10 applied to the substrate 12, which once again has the trench TR, and also the contact pads 26 with the bonding connections 24 and the contact 22.

In FIG. 10, instead of a cavity housing HG, provision is now made of a mold compound 30, which covers the substrate 12 with the bonding connections 24 and the contacts 26, while the trenches TR or the trench TR and the sensor layer 14 are open in order to be ready for the measurement. In this implementation, the trench TR is optional, but particularly advantageous in order to afford additional protection against further mechanical stresses.

The implementations of the semiconductor device 20 for low-vibration construction that are shown in FIGS. 8 to 10 are also combinable with the other implementations of the sensor chip 10 shown in FIGS. 1 to 5.

The invention claimed is:

1. A semiconductor device for measuring a hydrogen comprising:
  a sensor chip, the sensor chip comprising:
    a sensor comprising:
      a sensor layer,
        wherein a mechanical stress of the sensor layer changes upon contact with the hydrogen; and
      a membrane,
      wherein the sensor is configured to detect a change in the mechanical stress of the sensor layer by way of the membrane, wherein for detection purposes provision is made for exciting the membrane using a periodic signal.

2. The semiconductor device as claimed in claim 1, wherein one or more of:
  the sensor chip is configured as a MEMS chip, or
  the sensor layer is applied on the membrane.

3. The semiconductor device as claimed in claim 1, wherein the sensor is configured to cause the membrane to oscillate using the periodic signal to detect the change in the mechanical stress.

4. The semiconductor device as claimed in claim 3, wherein the sensor is configured to detect an oscillation property of the membrane, wherein the oscillation property is dependent on the change in the mechanical stress of the sensor layer.

5. The semiconductor device as claimed in claim 3, wherein the membrane is part of a capacitance, and
  wherein the sensor is configured to detect a change in the capacitance, wherein the change in the capacitance is dependent on the change in the mechanical stress of the sensor layer.

6. The semiconductor device as claimed in claim 5, wherein the sensor is configured to excite the membrane by applying an AC voltage to the capacitance.

7. The semiconductor device as claimed in claim 5, wherein the membrane is configured as an electrode of the capacitance, and wherein the sensor has at least one counter-electrode with respect to the membrane.

8. The semiconductor device as claimed in claim 5, wherein the membrane is arranged between two counter-electrodes.

9. The semiconductor device as claimed in claim 7, wherein the at least one counter-electrode is arranged between the membrane and a further membrane.

10. The semiconductor device as claimed in claim 1, wherein the detection of the change in the mechanical stress is effected by comparison with a further sensor, wherein a construction of a sensory layer of the further sensor differs from a construction of the sensor layer of the sensor.

11. The semiconductor device as claimed in claim 1, wherein a construction of the semiconductor device affords the sensor protection against further mechanical stresses.

12. The semiconductor device as claimed in claim 11, wherein the semiconductor device has further comprises:
    a deformable component configured to protect the sensor against further mechanical stresses.

13. The semiconductor device as claimed in claim 12, wherein the sensor chip has a substrate, on which the sensor is fitted, wherein the deformable component comprises a trench in the substrate, the trench at least partly surrounding the sensor.

14. The semiconductor device as claimed in claim 12, further comprising:
    a cavity housing having an opening, via which a cavity formed by the cavity housing is connected to an environment surrounding the semiconductor device; and
    wherein the deformable component comprises a wiring of the sensor chip.

15. The semiconductor device as claimed in claim 14, further comprising:
    a cavity housing having an opening, via which a cavity formed by the cavity housing is connected to an environment surrounding the semiconductor device; and
    wherein the deformable component comprises an adhesive connection of the sensor chip to a wall of the cavity housing.

16. The semiconductor device as claimed in claim 11, wherein a construction of the semiconductor device has potted regions of the sensor chip with an exposed sensor layer, wherein a coefficient of thermal expansion of a mold compound is configured to provide the sensor protection against thermally induced further mechanical stresses.

17. A method for measuring a hydrogen concentration in a medium using a semiconductor device, the semiconductor device comprising a sensor chip comprising a sensor, the sensor comprising a sensor layer and a membrane, a mechanical stress of the sensor layer changing upon contact with a hydrogen, the method comprising:
    contacting the sensor layer with the medium,
    detecting the change in the mechanical stress of the sensor layer using the sensor.

* * * * *